United States Patent [19]
Gardineer et al.

[11] 4,341,222
[45] * Jul. 27, 1982

[54] PATIENT SUPPORT APPARATUS FOR ULTRASOUND MAMMARY SCANNING APPARATUS

[75] Inventors: Bayard G. Gardineer, Skillman; James A. Heringes, Dayton, both of N.J.

[73] Assignee: Technicare Corporation, Solon, Ohio

[*] Notice: The portion of the term of this patent subsequent to Aug. 11, 1998, has been disclaimed.

[21] Appl. No.: 129,814

[22] Filed: Mar. 12, 1980

[51] Int. Cl.³ .............................................. A61B 10/00
[52] U.S. Cl. .................................................... 128/660
[58] Field of Search .............................. 128/660–663; 269/322–328

[56] References Cited
U.S. PATENT DOCUMENTS

| | | | |
|---|---|---|---|
| 3,083,376 | 4/1963 | Johns | 269/327 |
| 3,973,126 | 8/1976 | Redington et al. | 269/328 X |
| 4,059,098 | 11/1977 | Murdock | 128/660 |
| 4,167,180 | 9/1979 | Kossoff | 128/660 |
| 4,222,274 | 9/1980 | Johnson | 128/660 X |
| 4,233,988 | 11/1980 | Dick et al. | 128/660 |
| 4,252,125 | 2/1981 | Iinuma | 128/660 |

Primary Examiner—Henry J. Recla
Assistant Examiner—Francis J. Jaworski
Attorney, Agent, or Firm—Donal B. Tobin

[57] ABSTRACT

There is disclosed a patient support system for orienting the patient's breast and adjacent axilla region with respect to an ultrasound mammary scanning apparatus while the breast is suspended. A patient support platform is supported on top of a cabinet enclosing the ultrasound system which includes a transducer tank in which a transducer and sonic lens is submerged in water. The platform includes an aperture to permit the patient's breast to suspend into a pool of water defined by a flexible bag supported about the aperture by means of a frame. The bag drapes down and contacts the surface of the water in the transducer tank to provide a continuous transmission medium for the ultrasound from the transducer to the breast. The platform is specially contained to comfortably support the patient and restrain the patient against rolling or sliding. An adjustable headrest extends over the aperture and a step platform, kneeling bench and vanity screen, which can be converted to a support platform extension, permit different sized patients to conveniently use the apparatus.

22 Claims, 12 Drawing Figures

PATIENT SUPPORT APPARATUS FOR ULTRASOUND MAMMARY SCANNING APPARATUS

FIELD OF THE INVENTION

This invention relates to ultrasound imaging systems, especially adapted to perform diagnostic and screening imaging of the human breast and more particularly to a patient support system for orienting the patient's breast and adjacent axilla region with respect to the scanning equipment.

BACKGROUND OF THE INVENTION

Ultrasonic imaging has rapidly become a preferred modality for the non-invasive investigation of human tissues. Its non-ionizing character, moderate requirements in terms of signal processing and computation support, compactness, and continuing progress in image quality all favor the use of ultrasound whenever conditions permit. Thus, with the exception of body areas which are subject to uncontrolled multiple reflections (e.g. in the skull) and areas which fundamentally possess poor sonic transmission characteristics (e.g. the lungs), most areas of the body have been successfully made the subject of ultrasound diagnosis or screening. Some systems are multipurpose in essence, such as real time or B-scan body scanners and fetal monitors, while others are highly specialized, such as pulsed Doppler carotid imagers and flow monitors.

Recently, scientific and clinical data have been produced which provide strong indication of the efficacy of ultrasound scanning and imaging to screen, detect, and diagnose lesions in the human breast. In particular, it appears that appropriately directed and controlled B-scan images of a human breast permit detection of lesions in the 1 to 2 millimeter range and discrimination of malignancies in the 5 millimeter range based solely on ultrasound image. Further, such screening appears feasible at statistical levels of confidence comparable to those achieved through utilization of ionizing radiation (i.e., X-ray mammography). Such efficacy, together with ultrasound's apparent hazard-free nature, makes ultrasound a likely preferred modality for large scale screening programs for early detection of breast cancer.

Ultrasonic diagnosis of the human body using large aperture pulse-echo ultrasound imaging techniques have been described in, for example, U.S. Pat. Nos. 4,131,021 and 4,131,022 to Mezrich et al. Accordingly, such devices use a scanning transducer and an associated sonic lens submerged in water. The subject is positioned on an examination table over the water enclosure. Sonic energy from the transducer is transmitted through the water, focused by the sonic lens through the examination table and into the patient. Echoes are transmitted back in similar fashion. When diagnosing the condition of the human breast, it has been found desirable to eliminate the examination table from the transmission path and to transmit ultrasonic energy directly to the breast.

In certain instances, it has been found desirable to examine the human breast while it is suspended. It is also desirable to scan the axilla region adjacent the breast for lesions since it has been found that in a certain number of patients, lesions are found in this area. Accordingly, a primary object of the present invention is to provide a patient support system for orienting the patient's breast and the adjacent axilla region with respect to the scanning apparatus so that the breast may be examined while it is suspended.

SUMMARY OF THE INVENTION

The present invention relates to an apparatus for supporting a patient during diagnosis of a patient's breast and surrounding axilla region with an ultrasound imaging system. The support apparatus is particularly adapted to examining the breast while it is suspended. It is also adapted to comfortably support substantially all subjects regardless of their physique and breast size.

A patient support platform is supported on top of a cabinet enclosing the ultrasound system which includes a transducer tank in which a scanning transducer and an associated sonic lens are submerged in a fluid transmission medium, for example water. For convenience, the transmission medium will be identified as water throughout the application. However, those skilled in the art will appreciate that other transmission media can be used. The patient support platform includes an aperture in the surface against which the patient rests, which aperture is large enough to receive the patient's breast and surrounding axilla region. As will be subsequently described, cushioning is provided on the support platform to comfortably support and restrain the patient during the examination procedure. A cushioned headrest is movably supported on the patient support platform and may be adjusted to comfortably support the patient's head.

The platform rests on top of the cabinet and is connected to it by hinges so that it can be raised out of the way. Fixed over a portion of the top of the cabinet, under the platform, is a rigid splash tray with a well aligned with the aperture in the support platform. A flexible membrane, or bag, is supported about the well by means of a frame mounted in the splash tray.

The flexible bag contains a pool of water in which the patient's breast may be suspended during the diagnosis. The bag is designed so that it drapes down from its support frame and contacts the surface of the water in the transducer tank so as to provide a continuous transmission medium through which the ultrasound may be propagated from the transducer tank to the suspension pool. The bag forms the interface between the water in the transducer tank and the pool. It is, therefore, desirable that the bag be substantially ultrasonically transparent and that the temperature of the water in the transducer tank and the suspension pool be substantially the same so that there is little refraction of the ultrasonic waves as they propagate through the bag. However, it is possible to use a bag which does refract the propagating transmissions if the characteristics of the fluid transmission medium are adjusted to correct for this refraction. This could be accomplished by using different transmission media for the transducer tank and the suspension pool or by maintaining the temperature of the transmission medium in the transducer tank at a different level from that of the suspension pool or by other means known to those of ordinary skill in this art.

The bag and its support frame are mounted in the splash tray which forms part of the top scanner tank cabinet. The suspension pool defined by the bag is filled to the brim, so that the axilla can also be conveniently submerged in the pool. Thus, there is often spillage from the pool as the breast is introduced. The splash tray catches any such spillage. The splash tray is located under the patient support platform and includes a well bordered by an upstanding flange which is aligned with the aperture in the patient support platform. A bag support frame for the flexible bag is mounted in the well, permanently or removably by means of a mating flange which fits into the upstanding flange bordering the well. The bag support frame also includes a peripherally extending flange or wing which overlaps the edge of the well and extends down at an angle over a trough in the splash tray. Any overflow from the suspension pool will run down over the wing and into the trough to a drain. The upstanding flange about the well stands above the level of the trough so that water will not leak into the interior of the cabinet and damage the equipment in the cabinet.

This wing also serves as a lip over which the bag may be removably supported. The bag is fabricated from a flat sheet of plastic and gathered by an elastic cord placed in a peripheral hem. The cord gathers the bag to its proper shape, and the bag is then fitted over the lip of the wing in the fashion of a bonnet. The bag drapes down through the frame to form the suspension pool. When the bag is filled with water, it is held in contact with the frame through the combined effect of the elastic cord and the friction force between the bag material and the wing. In the area of the patient's torso, this wing is relatively narrow so as to accommodate the patient's body without obstruction. On the sides of the frame toward the patient's head, the wing is enlarged to provide a large surface area for contact with the bag material. The characteristics of the surface are especially adapted to provide a high friction contact between the bag and the surface to hold the bag against slipping. The edge of the wing may be provided with an elastomeric gasket to add further frictional engagement between the bag and the wing to hold the bag securely in place on the bag support flange while it is filled with water.

The shape of the well provided by the bag support frame is generally rectangular with a smooth radius at the corners. The smooth radius extends in both the plane parallel to the top of the housing and the plane perpendicular to the top of the housing, so that no sharp edge is in contact with the surface of the bag. When the bag is in place in the frame and the frame is in place in the splash tray, the bag may then be filled with water to provide a pool into which the patient's breast is suspended for examination. The bag projects down into the transducer tank and provides an interface between the water in the transducer tank and the water in the suspension pool. The configuration of this hem is specifically designed so that the bag drapes smoothly over the bag support frame without wrinkles, creases or folds.

As previously discussed, when the patient is in position with the breast suspended in the pool of water defined by the bag, the transducer tank is moved to align the transducer with the breast. Thus, the transducer tank moves with respect to the bag and will contact the bag at at least two points. It is desirable to include a low friction contact means between the edges of the tank and the bag to minimize the chance of damaging the bag. This low friction contact means can be a roller bearing supported on the edge of the tank in contact with the bag.

It is desirable, but not essential, that the suspension pool supported by the bag contain a smaller volume of water than the transducer tank and extend along the torso a greater distance than the tank so that it can conveniently receive the breasts of patients having different size torsos and so that it can receive different size breasts. The tank extends along the torso a shorter distance than the suspension pool, and the bag drapes over rollers on the transverse edges of the tank. Thus, the overall volume and, hence, the weight of the transducer tank may be kept within acceptable limits to facilitate easy movement of the transducer tank.

As previously explained, the scanning transducer and the associated sonic lens are housed within the scanning tank cabinet and cannot be seen by the operator. Thus, a window is provided in the side of the transducer tank so that the position of the transducer with respect to the breast may be viewed with a T.V. camera and displayed to the operator on a video screen at a control console. It is, therefore, desirable that the flexible bag be visibly transparent so that the T.V. camera can receive a good image of the breast. The bag is suspended from its frame so that in the region of the interface of the water in the transducer tank and the suspension pool, the bag is stretched tightly without wrinkles or folds so as to provide a window through which the T.V. camera can be focused on the breast and through which the ultrasound transmissions may be propagated.

The patient support platform is attached to the top of the scanner cabinet by means of hinges which permit the platform to tip up to expose the bag support frame and splash tray. The patient support platform includes an aperture aligned with the bag support frame. The platform is contoured in the vicinity of the aperture to support the patient and to closely overlap the bag support frame so that the patient's breast and surrounding axilla region may be conveniently submerged in the suspension pool. Cushioning is provided on the platform closest to the patient to allow patients of various physical size to be comfortably supported and properly oriented during breast examination. The patient may assume a standing kneeling or reclining position during the examination, as will be subsequently explained. The top of the examination platform is designed to accommodate the upper portion of the body in substantially the same way regardless of whether the patient is kneeling, standing or reclining. The patient's lower torso is supported near one end of the platform on a comfortable cushion which has upwardly projecting pillows on both sides of the patient's waist to restrain the patient from rolling while in position. The patient's upper torso is suspended across the aperture in the examination platform, and the patient's head rests on an adjustable headrest which can be moved toward or away from the patient's lower torso so that the head may be comfortably supported. A headrest is suspended over the aperture in the platform from structure fixed to the upper surface of the far end of the platform. This structure can be a plate having blocks which receive dowels extending from the headrest. A cover is provided on the far end of the platform to cover the headrest support structure and the headrest slides partially under this cover. Extending along both sides of the examination platform, adjacent the aperture, are cushion supports for the patient's arms and shoulders. These supports extend past the headrest. The portion of the cushion extending along the edge of the aperture is raised above the arm support so as to bear against the patient's rib cage and restrain the patient. The cushion is coated with a waterproof material which is comfortable to the skin.

Preferably, one breast is examined at a time, and the patient's arm adjacent the breast being examined is extended upwardly past the head and rested on the side cushion. The patient's other arm is folded comfortably on the top of the platform along the other side cushion. This permits the axilla region near the breast which is being examined to be exposed for diagnosis along with the breast. The position of the patient and the headrest are adjusted to permit this axilla region to be submerged in the suspension pool. Thus, the patient is comfortably supported in the head, waist, rib cage, shoulder and arm areas so that the breast and surrounding axilla region is conveniently displayed to the examination apparatus.

Accessories are provided in the form of a step platform, kneeling bench and fold down table top. In the folded position, the table top supports the patient's lower body so that the patient may be examined in the reclining position. If instead the patient prefers to stand on the step or kneel on the bench and bend over the examination platform, the table top may be folded up to provide a vanity screen so that the patient may be examined in private, out of the view of other people who may be present in the examination area. The kneeling bench may be slideably attached to the step platform so that it can be slid close to the cabinet during use or slid back against the vanity screen out of the way.

It can be seen that the patient support apparatus of the present invention provides an apparatus which comfortably supports patients of various sizes and properly orients the patient's suspended breast and surrounding axilla region during the examination.

Other features and advantages of the present invention will become apparent from the following detailed description of the preferred embodiment taken in conjunction with the following drawings.

BRIEF DESCRIPTION OF THE DRAWINGS

FIG. 9 shows a perspective view of the patient support platform and headrest;

FIG. 12 shows a detail of the support for the kneeling bench shown in FIG. 1.

DETAILED DESCRIPTION OF THE PREFERRED EMBODIMENT

Figure 1:
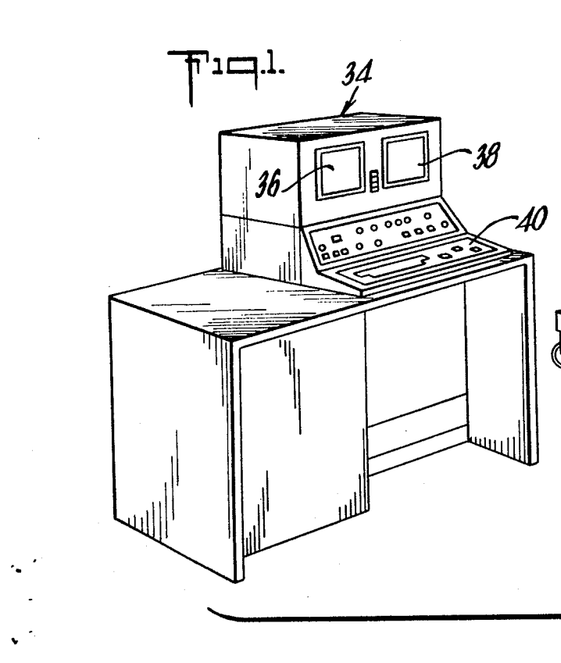
FIG. 1 shows the entire scanning apparatus, including the scanning tank cabinet, together with its associated patient support apparatus and the control console.

The present invention relates to a patient support apparatus for an ultrasound mammary scanning system. The overall system is shown in FIG. 1 and includes a scanning tank cabinet 10 enclosing an ultrasound system which includes a transducer tank 12 in which a scanning transducer 14 and associated sonic lens 16 are submerged in water. Cabinet 10 also encloses associated water circulation systems (not shown) and certain electrical circuitry (also not shown). A flexible bag 18 is suspended from a frame 78 (see FIG. 11) mounted in the top of cabinet 10 and contains a pool of water 20 in which the patient's breast may be suspended during diagnosis. A patient support platform 22 is supported on top of cabinet 10 and includes an aperture 24 in the surface against which the patient rests, which aperture 24 is large enough to expose the patient's breast and surrounding axilla region to the ultrasound system. A cushioned headrest 23 projects from under cover 15 over aperture 24 and may be adjusted by sliding it into or out of cover 15 on a support structure that will be described in greater detail in connection with FIG. 9. As shown in FIG. 9, patient support platform 22 is connected to cabinet 10 by hinges 25 so that it can be raised out of the way to expose the top of cabinet 10.

Referring again to FIG. 1, bag 18 drapes down across the top of transducer tank 12 to contact the surface of the water therein. Bag 18 is stretched tightly without wrinkles or folds so that it provides a window 26 at the interface 94 between the water in suspension pool 20 and transducer tank 12 so as to provide a continuous transmission medium through which the ultrasound may be propagated from transducer 14 into suspension pool 20 and, thus, to the patient's breast suspended in suspension pool 20.

An open area 27 (shown in FIG. 11) is contained within the back portion of cabinet 10 away from the patient. This open area 27 houses reservoirs, filters, circulation pumps and other parts of the water circulation system (not shown) for maintaining the water in transducer tank 12 and suspension pool 20 in the proper condition. Attached to the back of cabinet 10 is a control box 30 which contains electrical controls for the water circulation system (not shown) which maintains the water in transducer tank 12 and suspension pool 20 in the proper condition. A thermostatic water mixing assembly 32 is contained in a separate housing which is connected between scanning tank cabinet 10 and the available plumbing at the facility where the ultrasound mammary scanning apparatus is installed. A control console 34 houses the necessary circuitry and hardware components needed to operate and monitor the scanner system during an examination of a patient's breast. The incoming ultrasound echo signal from transducer 16 is electronically processed before it is displayed on CRT monitors 36, 38, or alternatively recorded on video tape or stored on X-ray film. The various functions of the system are microprocessor controlled, allowing for semi-automatic operation of the examination procedure and the manipulation and enhancement of the display image through the control panel 34 and associated keyboard 40.

Accessories 42 are provided to permit the patient to be comfortably oriented with respect to cabinet 10 in the standing, kneeling, or reclining position. If the patient is tall enough, the patient may merely stand at one end of cabinet 10 and lean over to rest the upper torso on patient support platform 22. For shorter patients, a step platform 44 is provided so that the patient may step up and then lean over the top of cabinet 10 resting the upper torso on patient support platform 22 in the same way. Alternatively, there is provided a kneeling bench 46 which may be used if the patient is more comfortable in the kneeling position. An upstanding screen 48 is attached to step platform 44 to provide a vanity screen for the patient. The top portion 50 is hinged at 51 so that it may be extended horizontally across stepping platform 44 and kneeling bench 46 to contact cabinet 10 to provide an extended table on which the patient may recline. The upper torso extends over support platform 22 in the same manner as though the patient were standing or kneeling. Vanity screen 48 includes a latch 53 to hold upper portion 50 in the upright position.

It can be seen from FIG. 12, that kneeling bench 46 is slideably attached to step platform 44 so that it may be placed close to cabinet 10 while in use or slid back against vanity screen 51 out of the way. The sliding mechanism includes a cylindrical tube 52 recessed in slot 53 extending along one edge of step platform 44. Linear slide bearings 54, fixed to the bottom of one leg 47 of bench 46, slide cooperatively along tube 52 to form a linear bearing. Detent 55 having rubber foot 56 extends from leg 47 of bench 46 and rests against the surface of step platform 44 to hold bench 46 in position so that it will not slide during use. A handle 57 is provided on the other leg 49 of bench 46. To move the bench, one grasps handle 57, and raises leg 59 of bench 46 off the surface of step platform 44. This pivots the bench about tube 52 and also raises detent 55 and rubber foot 56 away from the surface of step up platform 44. The bench can be slid between cabinet 10 and vanity screen 51 along the linear bearing provided by the cooperative action of tube 52 and slide bearings 54. The bench may then be lowered until leg 49 and detent 55 and foot 56 again engage the surface of step platform 44.

Figure 11:
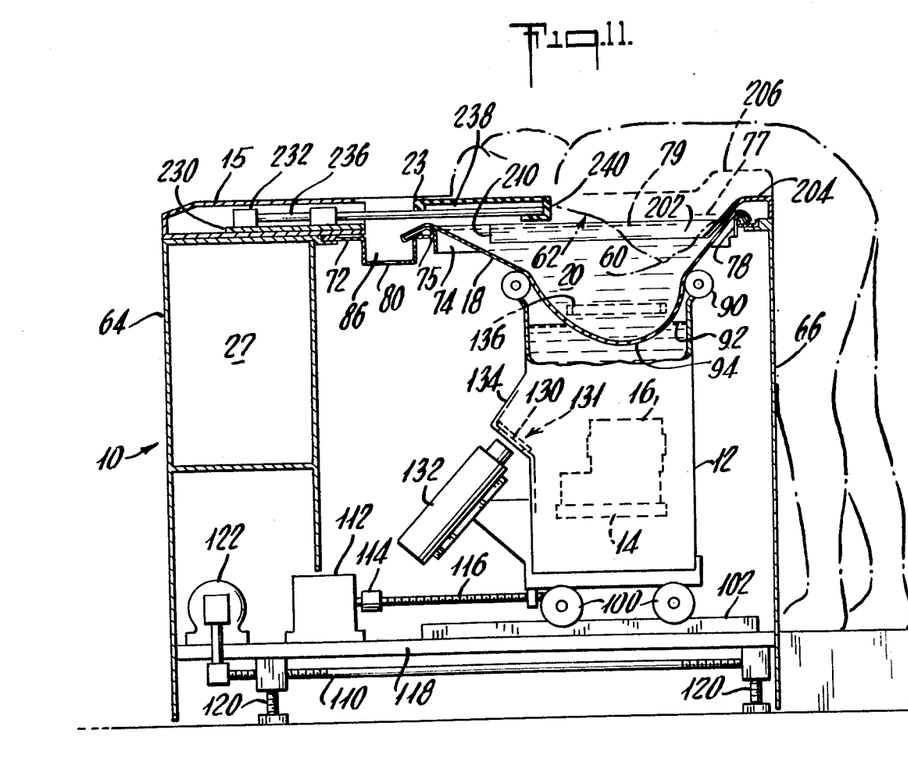
FIG. 11 shows an elevational view, partly in section, of the contents of the scanner housing.

Referring now to FIG. 11, the means for suspending the patient's breast and surrounding axilla region in suspension pool 20, properly oriented with respect to transducer tank 12, will now be described in greater detail. The patient is shown with the upper torso supported on platform 22 with the patient's breast 60 and adjacent axilla region 62 suspended through aperture 24 into suspension pool 20. As will be described in more detail in connection with FIG. 9, patient support platform 22 includes cushioning 200 to comfortably support and restrain the patient during the examination procedure. A cushioned headrest 23 is also movably supported with respect to examination platform 22 and may be adjusted to comfortably support the patient's head.

Referring again to FIG. 1 and FIG. 11, cabinet 10 is a generally rectangular enclosure having vertical end walls 64 and 66 and side walls 68 and 70. The top of cabinet 10 is fixed about upper periphery of walls 64, 66, 68 and 70 and a portion of the top functions as a splash tray 72. Splash tray 72 includes a well 74 defined by an upstanding flange 76 aligned generally about the periphery of aperture 24 in patient support platform 22. Mounted in well 74 is bag support frame 78. Bag support frame 78 may be permanently bonded to upstanding flange 76 or may be pressed tightly into well 74 formed by upstanding flange 76 and sealed with a peripheral gasket 75 made of some sealing material like rubber.

Bag support frame 78 includes a peripherally extending flange or wing 80 which overlaps the edge of upstanding flange 76 of well 74. Wing 80 also serves as a lip over which bag 18 may be removably supported. As will be explained subsequently, bag 18 is fabricated from a flat sheet of plastic and gathered by an elastic cord 82 placed in a peripheral hem 84 about the periphery of bag 18. The cord gathers the bag into the shape of a bonnet, and the bag is then fitted over the lip of wing 80 and held in place.

Figure 2:
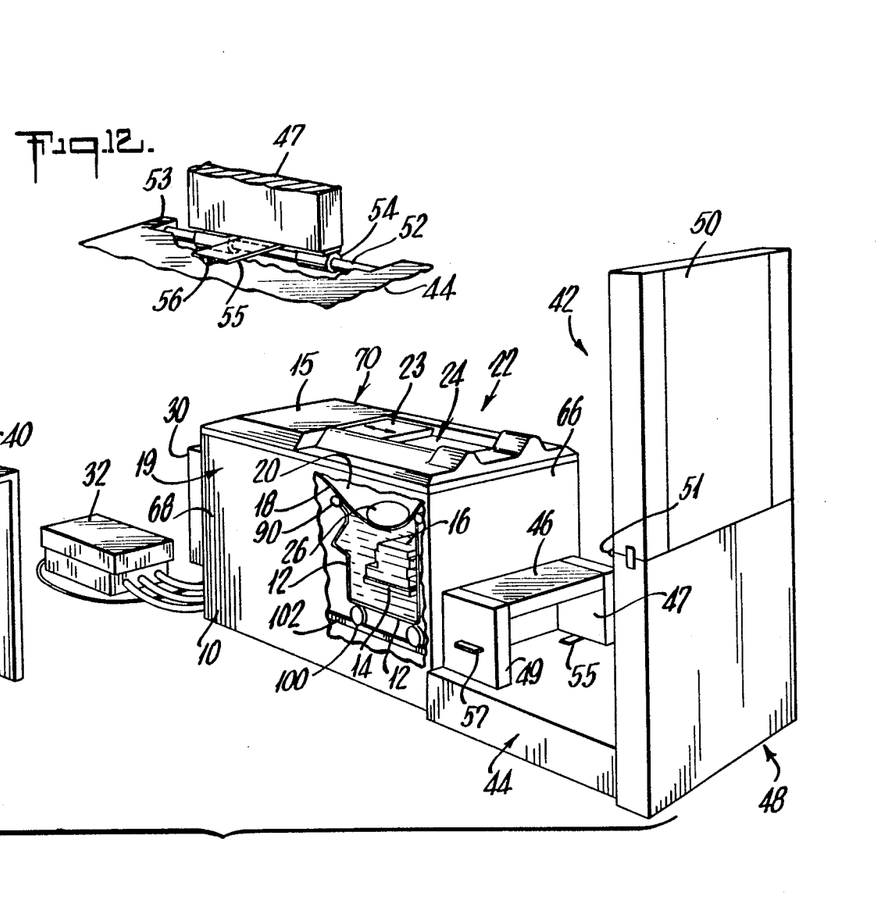
FIG. 2 shows a plan view of the splash tray of the present invention.
Figure 4:
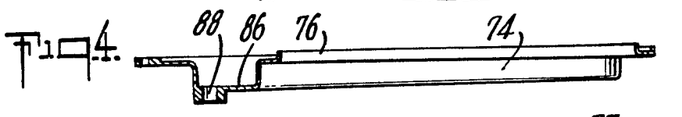
FIG. 4 shows a sectional elevation of the splash tray of FIG. 2 taken along line 4—4.

As can be seen in FIG. 11, the bag drapes down through bag support frame 78 over the edges of transducer tank 12 to provide a means for containing suspension pool 20. Since the suspension pool is filled to the brim of bag support frame 78 so that the axilla can be conveniently submerged in suspension pool 20, there may be spillage from pool 20 as the breast is introduced. Consequently, splash tray 72 is designed to provide a means under the patient support platform to catch any such spillage. It can be seen, particularly in FIG. 11, that splash tray 72 is provided by a trough 86 running about the periphery of well 74. Wing 80 of bag support frame 78 overlaps the edge of well 74 and extends down at an angle over the trough 86 in the splash tray 72. Any overflow from suspension pool 20 will run down over wing 80 into trough 86 to a drain 88 shown particularly in FIGS. 2 and 4. Drain 88 may be connected by suitable means to proper disposal means located in the facility where the scanning unit is installed.

Figure 3:
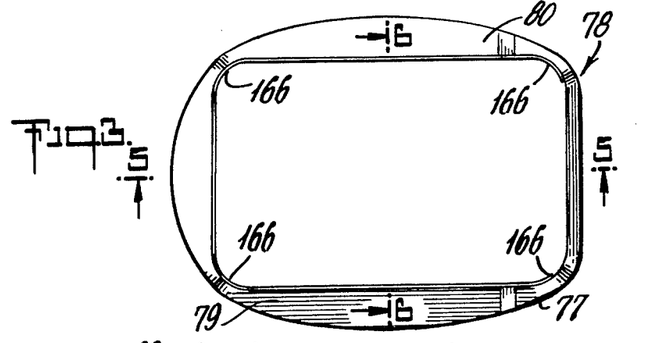
FIG. 3 shows a plan view of the bag support frame.
Figure 5:
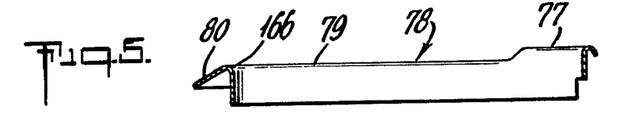
FIG. 5 shows a sectional elevation of the bag support frame of FIG. 3 taken along line 5—5.

It can be seen from FIGS. 3, 5 and 11 that the portion 77 of frame 78 closest to the patient's waist is higher than the portion 79 removed from the patient's waist. Also, the width of wing 80 is greater at portion 77 than at portion 79. Thus, when the breast is introduced into suspension pool 20, almost all of the resulting spillage will go over the front of frame 78 over the wider portion of wing 80. Trough 86 is designed to accommodate more spillage from the front of frame 78. The forward portion of trough 86 removed from the patient's waist is deeper than the rear portion closest to the patient's waist. Spillage will flow toward the deeper end of trough 86 and out through drain 88.

Still referring to FIG. 11, it can be seen that bag 18 contacts the upper edges of transducer tank 12 at a smooth, low-friction surface preferably provided by roller bearing 90 supported at the upper edge of transducer tanks 12 and oriented transverse to the body of the patient. It can be seen that the bag provides an interface 94 between the water in suspension pool 20 and the water in transducer tank 12. The weight of the water in suspension pool 20 stretches the bag 18 and pushes it somewhat below the surface 92 of the water in transducer tank 12 so as to provide a window 26 (see FIG. 1) which is stretched tightly without wrinkles or folds.

Transducer tank 12 is mounted on wheels 100 which ride in tracks 102. A transducer tank drive mechanism 110 is housed within cabinet 10 and is shown schematically in FIG. 11 to include a drive motor 112, a transmission means 114 connected to the output of drive motor 112, and a lead screw 116 connected between transmission 114 and transducer tank 12. Also in FIG. 11, it is shown that the entire transducer tank 12 is mounted on a platform 118 which may be raised and lowered by means of jacks 120 located near the corners of the platform. Jacks 120 are motor driven by means of motor 122 and associated drive and transmission means shown only schematically.

Thus, transducer tank 12 can be moved vertically with platform 118 or translated along patient's torso to align transducer 14 and sonic lens 16 with the patient's breast as it is suspended in pool 20. The use of low friction rollers 90 on the upper edges of tank 12 permits the shape of bag 18 to easily change as tank 12 moves.

Since the transducer 14 and associated sonic lens 16 are housed within cabinet 10 and cannot be seen by the operator, a window 130 is provided in the side of transducer tank 12 so that the position of the transducer 14, with respect to the patient's breast, may be viewed with T.V. camera 132 and displayed on video screen 36 or 38 at control console 34. To avoid distortion, window 130 is preferably mounted in a cup-shaped frame 134 bolted about an opening 131 in the side of transducer tank 12. Window 130 is properly sealed into frame 134, and frame 134 is properly sealed to the side of tank 12 with suitable gaskets so that water does not leak out of transducer tank 12. Lights 136 are provided along the top of tank 12 to provide proper illumination for T.V. camera 132. Flexible bag 18 permits pool 20 to be shifted as transducer tank 12 moves so that window 26 is maintained at interface 94 between the water in pool 20 and in transducer tank 12. T.V. camera 132 focuses through window 130 and interface window 26 into pool 20 so that the operator can determine when transducer 14 and sonic lens 16 are properly positioned under breast 60. The operator can then stop the motion of transducer tank 12 and be assured that the scanning apparatus is properly positioned with respect to the patient's breast. It will be noted that suspension pool 20 contains a smaller volume of water than tank 12 but that pool 20 extends a greater distance along the patient's torso so that it can conveniently receive breasts of patients with different size torsos and so that it can receive different size breasts. Tank 12 extends along the torso only a short distance, and bag 18 drapes over rollers 90 on the transverse edges of tank 12. The cooperative effect of using pool 20 and tank 12 allows the present scanning system to be quickly adapted to different size patients by merely moving tank 12 into position. As tank 12 moves, the shape of pool 20 automatically adjusts so that the patient's breast is always completely suspended in pool 20 and does not rest on or too close to the sides of pool 20. Thus, the use of a moveable tank 12 and a flexible pool 20 provides a versatile and quickly adjustable means for examining patient's breasts while in the suspended condition.

Flexible bag 18 containing suspension pool 20, in which the patient's breast is suspended, is designed to drape down from its support frame 78 and contact the surface 92 of the water in transducer tank 12 so as to provide a continuous transmission medium through which the ultrasound may be propagated from transducer tank 12 to the patient's breast. It is, therefore, desirable that bag 18 be substantially ultrasonically transparent and that the temperature of the water in transducer tank 12 and suspension pool 20 be substantially the same so that there is little refraction of the ultrasonic waves as they propagate through the bag. However, as previously discussed, it is possible to use bags which do refract the propagating transmissions if the characteristics of the fluid transmission medium are adjusted to correct for this refraction. This could be accomplished by using different transmission media for transducer tank 12 and suspension pool 20 or by maintaining the temperature of the transmission medium in transducer tank 12 at a different level from that of the medium in suspension pool 20.

Figures 7, 8:
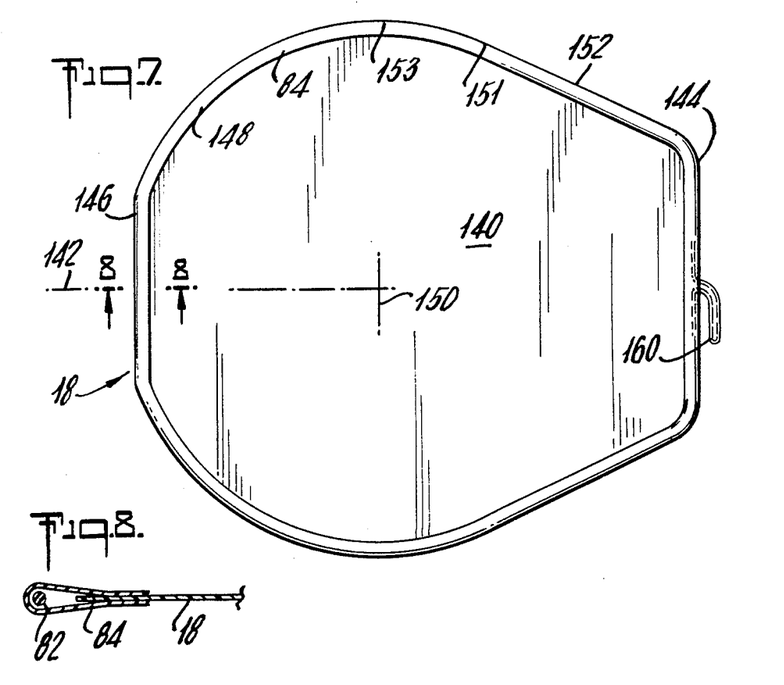
FIG. 7 shows a plan view of the bag.
FIG. 8 shows a sectional detail of the bag shown in FIG. 7 taken along line 8—8.

Referring now to FIG. 7, the details of flexible bag 18 will now be described. Bag 18 is formed from a flat sheet 140 of a high-strength plastic which is both visibly and ultrasonically transparent. We have found that a polyester-based thermoplastic polyurethane film or sheet, sold under the trandemark TUFTANE* by B. F. Goodrich, General Products Co. of Akron, Ohio, provides a suitable bag. The bag is cut from a flat sheet and is substantially symmetrical about a longitudinal axis 142. A portion 144 of the bag, which will be supported on frame 78 near the waist of the patient when the bag is in use, extends at substantially right angles to center line 142 for a distance greater than the transverse width of generally rectangular well 74 in which frame 78 is supported. A transverse portion 146, located opposite portion 144 away from the patient's waist while the bag is in use, extends transversely from center line 142 for a distance less than portion 144 extends. Portion 148 is formed by the arc of a circle generated about center 150 and extends from the end of portion 146 to point 151 a short distance past the point 153 where the vertical radius from center 150 intersects the circumference of the circle generated about point 150. Portion 152 extends from the end of portion 144 in a straight line to point 151. Thus, it can be seen that bag 18 is formed at its forward end by a circle which is cut off along portion 146. The circle extends into a trapezoidally-shaped portion whose minor base is formed by portion 144.
*Trademark Referring now to FIG. 8, it can be seen that a hem 84 is formed about the border of sheet 140. Hem 84 may be formed by a separate piece of plastic or compatible material which may be easily bonded or sewn to sheet 140. Alternatively, hem 84 may be formed by merely folding over a portion of the periphery of sheet 140 and heat sealing the folded over portion to sheet 140 to form hem 84. Disposed within hem 84 is an elastomeric cord 82 which extends about the entire periphery of sheet 140 and draws the sheet into a bonnet. Referring again to FIG. 7, there is shown a tab 160 which is used to orient the sheet so that it may be correctly placed over frame 78.

Figure 10:
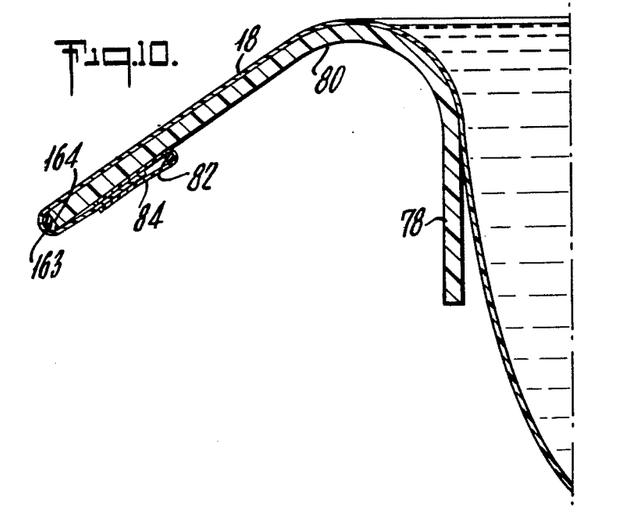
FIG. 10 shows a detailed view of the bag support frame of FIG. 3.

Referring now to FIG. 10, it can be seen that bag 18 fits smoothly against the upper surface of frame 78. Elastomeric cord 82 and hem 84, in which cord 82 is confined, tuck under the edge of wing 80, and the body of bag 18 extends up over wing 80, through frame 78 and drapes down through well 74 to provide a support for suspension pool 20. When the water is placed in bag 18 to form pool 20, bag 18 is pulled tightly and drapes substantially without folds or wrinkles. Bag 18 is held against slipping through the combined effect of elastic cord 82 and the frictional force between the bag material and wing 80. The upper surface of wing 80 is preferably provided with a high co-efficient of friction so as to provide a high holding force for bag 18. Alternatively, at least a peripheral portion of sheet 140, which contacts wing 80 and frame 78, can be provided with a high-friction surface to further provide a holding force for bag 18. In an alternative embodiment, a rubber gasket 163 may be provided about the peripherally extending edge 164 of wing 80 to provide still further frictional holding force for bag 18.

Figure 6:
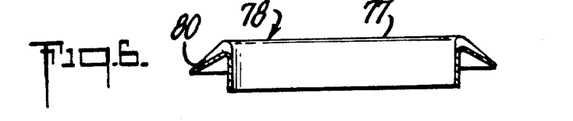
FIG. 6 shows a sectional elevation of the bag support frame of FIG. 3 taken along line 6—6.

Referring now to FIGS. 3, 5 and 6, it can be seen that the shape of bag support frame 78 is generally rectangular and includes smooth radii 166, which radii extend in both the plane parallel to the top of cabinet 10 and the plane perpendicular to the top of cabinet 10 so that no sharp edge is in contact with the surface of bag 18.

Referring now to FIGS. 9 and 11, cushioned patient support platform 22 and headrest 23 will now be discussed. Support platform 22 is hinged to the sidewall 70 at cabinet 10 so that it may be lifted out of the way. Patient support platform 22 includes a centrally disposed aperture 24 aligned generally with the bag support frame 78. Platform 22 extends along the entire top of cabinet 10 from end wall 66 near the patient's waist to end wall 64 removed from the patient's waist. Consequently, platform 22 covers open area 27 in which various elements of the water circulation system (not shown) are housed. Platform 22 is contoured in the vicinity of aperture 24 to support the patient and to closely overlap bag support frame 78 so that the patient's torso may be supported so that the breast and surrounding axilla region may be conveniently submerged in pool 20. The contours are shown best in FIG. 9. The overlapping relationship is shown best in FIG. 11.

Referring now to FIG. 9, it can be seen that platform 22 has armrests 29 extending along the sides. Inside armrests 29, and extending along both sides of aperture 24, and raised rib cage supports 202. Rib cage supports 202 are spaced apart a sufficient transverse distance to support the patient's rib cage area as the patient lays on top of platform 22 so that one breast can be comfortably suspended through aperture 24 into pool 20. It can be seen that the outside of rib cage supports 202 slopes up to a rounded peak and then slopes down into aperture 24 so that the patient's body may be supported close to the surface of the water in pool 20. In the area of the patient's waist, the contour of platform 22 is raised above the level of rib cage supports 202 to form a stomach support 204 which supports the patient's stomach as the patient suspends the torso over aperture 24. On each side of stomach support 204, the contour of platform 22 rises up further to form side supports 206 and 208 to engage the sides of the patient's lower torso to restrain the patient against rolling. Side supports 206 and 208 slope up from armrests 29 more sharply than rib cage supports 202 to a rounded tip and then slope down into aperture 24. The inside face of stomach support 204 also slopes down into aperture 24.

As shown back in FIG. 11, rib cage supports 202, stomach support 204 and side supports 206 and 208 are hollow and overlap bag support frame 78. The downwardly sloping surfaces of rib cage supports 202, stomach support 204 and side supports 206 and 208 extend down below the upper edge 77 of bag support frame 78 almost to the surface of the water in pool 20 so that the patient's body may be supported close to the surface of the water in pool 20.

Openings 210 are provided in the downwardly sloping surfaces of rib cage supports 202 to accommodate the end of frame 78 away from the patient's waist. The end of frame 78 closest to the patient's waist is enclosed within hollow stomach support 204 and side supports 206 and 208. The entire surface of armrests 29, rib cage supports 202, stomach support 204 and side supports 206 and 208 are cushioned with a suitable cushioning material like a soft, polyurethane foam coated with a water-resistant skin.

Headrest 23 and its support structure will now be described in conjunction with FIG. 9. Mounted on the surface of support platform 22, adjacent aperture 24, opposite stomach support 204, is a metal headrest support plate 230. Four bearing blocks 232 are welded to plate 230 and include a U-shaped opening 234 facing plate 230. Dowels 236 are fixed to a headrest support 238 and extend through openings 234 in blocks 232 to provide a linear bearing for headrest 23 so that it may be moved longitudinally along the patient's body over aperture 24 to properly support the patient's head. A headrest cushion 240 is fitted to headrest support 238. The side edges 242 of headrest cushion 240 are contoured to fit against the downwardly sloping surfaces of rib cage supports 202. Headrest cushion 240 may also be made of soft polyurethane foam covered with a water-resistant skin. As can be seen best in FIG. 11, headrest cushion 240 projects from its support over aperture 24 and obscures any exposed portions of bag support frame 78 or splash pan 72. Thus, the patient sees only the surface of the water in pool 20 and the contoured, cushioned surfaces of support platform 22 and headrest 23.

Top cover 15 fits over the far end of platform 22 removed from the patient's waist and obscures the headrest support structure from view. The end of cover 15 which faces aperture 24 is open so that headrest 23 may slide on its support structure from underneath cover 15.

When patient support platform 22 is in place on top of cabinet 10, aperture 24 is aligned generally about frame 78. Frame 78 is mounted within well 74 of splash tray 72. Splash tray 72 is mounted on the portion of the top of cabinet 10 closest to the patient and extends between end wall 66 and the top of chamber 27. Bag 18 is formed into a bonnet and put in place over wing 80 of frame 78 and allowed to drape down through well 74 into contact with the surface of the water in tank 12. The weight of the water in suspension pool 20 stretches bag 18 so that it provides a smooth, wrinkle-free window 26 (See FIG. 1) at the interface of the water in tank 12 and pool 20 so that a continuous transmission medium is provided for the ultrasound transmissions from transducer 14 through sonic lens 16 through the water in tank 12 through window 26 provided by bag 18 through suspension pool 20 and into the patient's breast.

In use, the patient has a choice of standing at the end of cabinet 10 and merely leaning over patient support platform 22 or may step onto platform 44 or kneel on bench 46 or recline on the table formed when the top part 50 of vanity screen 48 is folded down into contact with cabinet 10. For the purposes of illustration of the use of the present patient support apparatus, it will be assumed that the patient merely stands at the end of the cabinet and leans over the top. The patient's lower abdomen is supported on stomach support 204, and the sides of the patient's lower torso bear against side supports 206 and 208 to restrain the patient from rolling. The patient's rib cage rests against rib cage supports 202 to further provide a vertical support for the patient and restraint against rolling. The patient's head rests on headrest cushion 240 which can be adjusted to comfortably fit the particular patient. The patient's body is twisted slightly to the side so that only one breast suspends through aperture 24 in patient support platform 22. The arm adjacent the breast which is being examined may be extended up above the head and rested along the inside of the pertinent rib cage support 202 to expose the axilla region adjacent the breast which is being examined. The patient's other arm lays comfortably along the armrest 29, folded in a comfortable position. As the breast and surrounding axilla region are suspended into suspension pool 20, there is apt to be some spillage of the water from pool 20 over the forward portion of wing 80 into trough 86. Because the rearward position of frame 78 closest to the patient's waist is raised, it is unlikely that much spillage will occur in this area. Consequently, the trough in this area is smaller. Once the patient is in position on patient support platform 22, the operator turns on T.V. camera 132 and its illumination light 136 to obtain a picture on CRT monitor 36 or 38 of the patient's breast through window 130 in the side of tank 12 and through interface window 26 provided by bag 18. The operator, while looking at the T.V. picture, moves transducer tank 12 until the patient's breast comes into alignment with transducer 14 and lens 16. The operator then stops the movement of the tank, knowing that the breast and the ultrasonic transducer are properly aligned so that an ultrasonic mammary scan may begin. It will be appreciated that as transducer tank 12 moves, the shape of suspension pool 20 changes as bag 18 rolls along rollers 90. Thus, the present scanning apparatus can be easily adjusted to accommodate patients with different size torsos. The breasts of very tall patients will be located further from the end of cabinet 10 than those of short patients. It requires only a momentary adjustment of the scanning apparatus to accommodate the scanning apparatus to different size patients.

The present invention has been described in conjunction with the preferred embodiment. Those skilled in the art will appreciate that many modifications and changes may be made to the preferred embodiments without departing from the present invention. It is, therefore, not intended to limit the present invention except as set forth in the appended claims.

What we claim is:

1. Apparatus for supporting a patient during examination of the patient's breast comprising:
   a tank for containing a quantity of fluid transmission medium;
   a sonic energy transducer disposed in said tank for transmitting to and receiving sonic energy from the patient;
   a patient support platform for supporting the patient's upper body over said tank;
   said platform having an aperture therethrough for receiving the patient's breast;
   readily changeable and disposable flexible bag means having an open end supported adjacent said platform and about said aperture and having a closed end adapted to be draped into engagement with fluid in said tank;
   said bag means adapted to contain a quantity of fluid to define a pool of fluid into which the patient's breast may be suspended without contacting said bag during diagnosis;
   said bag means adapted to form an interface between fluid in said pool and fluid in said tank;
   the transmission properties of said bag means permitting transmission of sonic energy from said transducer therethrough without substantial distortion of said sonic energy.

2. Apparatus for supporting a patient during examination of the patient's breast comprising:
   a tank for containing a quantity of fluid transmission medium;
   a sonic energy transducer disposed in said tank for transmitting to and receiving sonic energy from the patient;
   a patient support platform for supporting the patient's upper body over said tank;
   said platform having an aperture therethrough for receiving the patient's breast;
   flexible bag means having an open end supported adjacent said platform and about said aperture and having a closed end adapted to be draped into engagement with the fluid in said tank;
   said bag means including;
   a body;
   a hem about the periphery of said body adapted to receive an elastomeric cord for gathering the periphery of said body to form a bag;
   said hem including a positioning means for orienting said bag properly with respect to the patient;
   said bag adapted to contain a quantity of fluid to define a pool of fluid into which the patient's breast may be suspended without contacting said bag during diagnosis;
   said bag forming an interface between fluid in said pool and fluid in said tank;
   the transmission properties of said bag permitting transmission of sonic energy from said transducer therethrough without substantial distortion of said sonic energy.

3. The apparatus of claim 2 further including:
   orienting and restraining means disposed on said platform about the periphery of said aperture for orienting the patient's torso close to the surface of said fluid in said pool and for restraining the patient from rolling or sliding on said platform.

4. The apparatus of claim 3 further including armrest means extending along the sides of said platform outside said orienting and restraining means for supporting one or both of the patient's arms during diagnosis of the patient's breast.

5. The apparatus of claim 3 wherein said orienting and restraining means include a ridge raised above said platform, extending at least partially about said aperture and having:
   a stomach support section extending along the edge of said aperture close to the patient's waist;
   side support sections disposed on opposite transverse sides of said stomach support section and projecting upwardly thereabove to bear against the sides of the patient's lower torso to thereby restrain the patient from rolling or sliding off said platform;
   rib cage support sections extending along the sides of said aperture axially of said torso and having a surface sloping toward the surface of the fluid in said suspension pool.

6. The apparatus of claim 3 wherein said orienting and restraining means includes a hollow ridge raised above the plane of said platform and extending at least partially about said aperture, and having a surface sloping from said ridge into said aperture to permit the patient's body to be supported close to the surface of the fluid in said pool;
   and further including a bag support frame having a circumferential wall defining an opening through which said bag means drapes and having a peripheral flange extending outwardly from said wall to provide a lip for holding said bag means on said frame;
   said raised hollow ridge at least partially overlapping said frame wall and said frame flange so that the surface of the fluid in said pool defined by said bag means may be disposed close to the patient's torso.

7. The apparatus of claim 6 further including headrest means mounted on said platform and projecting over said aperture;
   a headrest cushion supported on said headrest means and including tapered edges mating with the confronting sloping surfaces of said raised ridge.

8. The apparatus of claim 2 further including:
   a bag means support frame having a circumferential wall defining a generally rectangular opening through which said bag means drapes and having a peripheral flange extending outwardly from said wall and sloping away from the surface of said platform;
   said flange forming a lip for holding said bag means on said frame.

9. The apparatus of claim 8 wherein said frame wall and said frame flange include smoothly blended surfaces confronting said bag means to permit said bag means to drape substantially without folds or creases and without engaging any sharp corners.

10. The apparatus of claim 8 wherein a portion of said bag means support frame near the patient's waist is raised above the opposing end of said frame so that as the patient's breast is introduced into the pool supported by said bag, any resulting overflow will be away from said raised portion.

11. The apparatus of claim 2 further including: headrest means slideably mounted on said platform and projecting over said aperture for supporting the patient's head while the patient's breast is suspended into said aperture.

12. The apparatus of claim 11 wherein said headrest means includes:
    a support plate mounted on said patient support platform;
    bearing blocks mounted on said plate;
    dowel means slideably engaging said bearing blocks;
    a headrest fixed to said dowel means; and,
    a cushion mounted on said headrest whereby said headrest may move longitudinally along the patient's body so that the heads of patients with different size torsos may be supported while the upper torso is suspended into said aperture.

13. Apparatus for examining a patient's breast while the patient is suspended in an ultrasound transmission medium with respect to an ultrasound imaging system having a sonic energy transducer submerged in a tank of fluid transmission medium, said apparatus comprising:
    a generally horizontally disposed bag support frame defining an aperture adapted to receive the patient's breast;
    a flexible bag supported by said frame and draping through said aperture for containing a quantity of fluid to define a pool in which the patient's breast may be suspended without contacting said bag during diagnosis;
    said bag adapted to drape through said aperture and contact the surface of the fluid transmission medium in said tank and to provide an interface between said transmission pool and said tank;
    said bag including;
        a body;
        a hem about the periphery of said body, adapted to receive an elastomeric cord for gathering the periphery of said body to form a bag;
    said hem including a positioning means for orienting said bag with respect to patient;
    said bag adapted to be stretched tightly by the fluid in said suspension pool to provide a window at said interface through which ultrasound transmissions may be propagated.

14. The apparatus of claim 13 further including rollers adapted to contact the surface of said bag as it drapes through said aperture.

15. The apparatus of claim 13 wherein said bag support frame includes an upstanding circumferential flange and a surrounding peripheral wing extending out from said flange and down at an angle to the horizontal;
    said wing having a substantial surface area and providing a lip about which said bag may be stretched like a bonnet.

16. Apparatus for supporting a patient during examination of the patient's breast comprising:
    a tank for containing a quantity of fluid transmission medium;
    a sonic energy transducer disposed in said tank for transmitting to and receiving sonic energy from the patient;
    flexible bag means having an open end supported adjacent said platform and about said aperture and having a closed end adapted to be draped into engagement with the fluid in said tank;
    said bag means adapted to contain a quantity of fluid to define a pool of fluid into which the patient's breast may be suspended during diagnosis;
    said bag means adapted to form an interface between fluid in said pool and fluid in said tank;
    the transmission properties of said bag means permitting transmission of sonic energy from said transducer therethrough without substantial distortion of said sonic energy
    a splash tray under said patient's support platform and about said aperture having a well therein generally aligned with said platform aperture;
    an upstanding flange surrounding the circumference of said well;
    a trough on said splash tray for receiving water that may spill from said pool contained by said bag means;
    a bag support frame mounted in said well and defining an opening aligned with the areas of the patient which examined and having a downwardly depending flange cooperating with said upstanding well flange to provide sealing engagement therebetween;
    generally, circumferential wing means extending from said frame over said trough and down from said patient's support platform to guide any spillage from said pool into said trough.

17. The apparatus of claim 16 wherein said wing means includes a surface area projecting outwardly from said opening and downwardly from the patient support platform to provide a frictional contact surface for said bag means, and the under sides of said wing means cooperates with the surface of said wing means to provide a lip over which the periphery of said bag means may be stretched like a bonnet to hold said bag means in place.

18. The apparatus of claim 17 wherein the edge of said wing means further includes a high friction gasket to provide additional holding force for said bag means.

19. The apparatus of claim 16 wherein said trough completely surrounds said bag support frame and becomes deeper from a narrow portion near the patient's waist to a wide portion removed from the patient's waist.

20. Apparatus for supporting a patient during examination of the patient's breast comprising
    a tank for containing a quantity of fluid transmission medium;
    a sonic energy transducer disposed in said tank for transmitting to and receiving sonic energy from the patient;
    flexible bag means having an open end supported adjacent said platform and about said aperture and having a closed end adapted to be draped into engagement with the fluid in said tank;
    said bag means adapted to contain a quantity of fluid to define a pool of fluid into which the patient's breast may be suspended during diagnosis;

said bag means adapted to form an interface between fluid in said pool and fluid in said tank;

the transmission properties of said bag means permitting transmission of sonic energy from said transducer therethrough without substantial distortion of said sonic energy; and, a patient support accessory unit adapted for use during a diagnosis comprising:

a step platform;

a kneeling bench slideably mounted on said step platform to permit said bench to be positioned near the patient support platform or to permit said bench to be stored out of the way or removed from said patient support platform; and, a vanity screen attached to said step platform removed from said support platform.

21. The apparatus of claim 20 wherein said vanity screen includes a lower portion and an upper portion hingeably supported on said lower portion and adapted to fold down over said step platform and contact said support platform to provide a table on which the patient may recline during the examination.

22. The apparatus of claim 20 wherein said slideably mounted kneeling bench includes:

a tubular bearing member fixed along one side of said step platform;

annular bearing means fixed to said bench and slideably engaging said tubular member to provide a linear bearing;

a slide stop projecting from said bench and frictionally engaging the surface of said step platform to stop said bench from sliding on said linear bearing.

* * * * *

UNITED STATES PATENT AND TRADEMARK OFFICE
CERTIFICATE OF CORRECTION

PATENT NO. : 4,341,222
DATED : July 27, 1982
INVENTOR(S) : Bayard G. Gardineer et al.

It is certified that error appears in the above-identified patent and that said Letters Patent are hereby corrected as shown below:

At Column 15, line 30, "patient" should be -- breast --.

Signed and Sealed this

Twelfth Day of October 1982

[SEAL]

Attest:

GERALD J. MOSSINGHOFF

Attesting Officer  Commissioner of Patents and Trademarks